United States Patent [19]

Brower

[11] Patent Number: 4,646,731

[45] Date of Patent: Mar. 3, 1987

[54] SELF ADHESIVE SUTURE AND BANDAGE

[76] Inventor: Arthur B. Brower, P.O. Box 480145, Los Angeles, Calif. 90048

[21] Appl. No.: 735,589

[22] Filed: May 20, 1985

[51] Int. Cl.$^4$ .............................................. A61F 13/00
[52] U.S. Cl. ..................................... 128/156; 604/304
[58] Field of Search ........................ 128/155, 156, 157; 604/304, 308; 206/440, 441

[56] References Cited

U.S. PATENT DOCUMENTS 4,192,299 3/1980 Sabatano ............................. 128/155
4,418,822 12/1983 Dotta ................................... 128/155

Primary Examiner—Henry A. Bennet
Attorney, Agent, or Firm—I. Louis Wolk

[57] ABSTRACT

A novel type of self adhesive suture or bandage is described wherein the adhesive coated surface is protected against contact at its edges by means of folded protective strips providing tabs for removal of individual units from a protective backing and application to an incision or wound while avoiding contact of fingers or forceps with any portion of the adhesive coating.

7 Claims, 7 Drawing Figures

U.S. Patent     Mar. 3, 1987     4,646,731
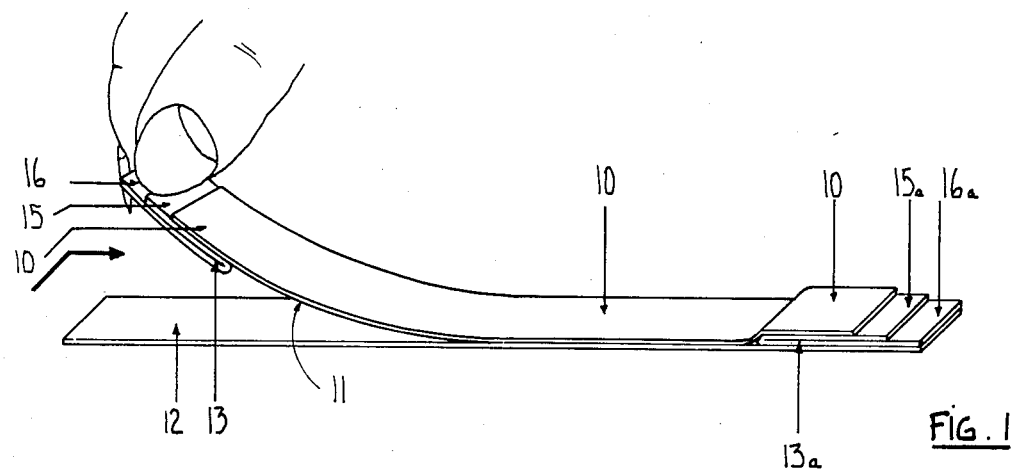
Fig. 1
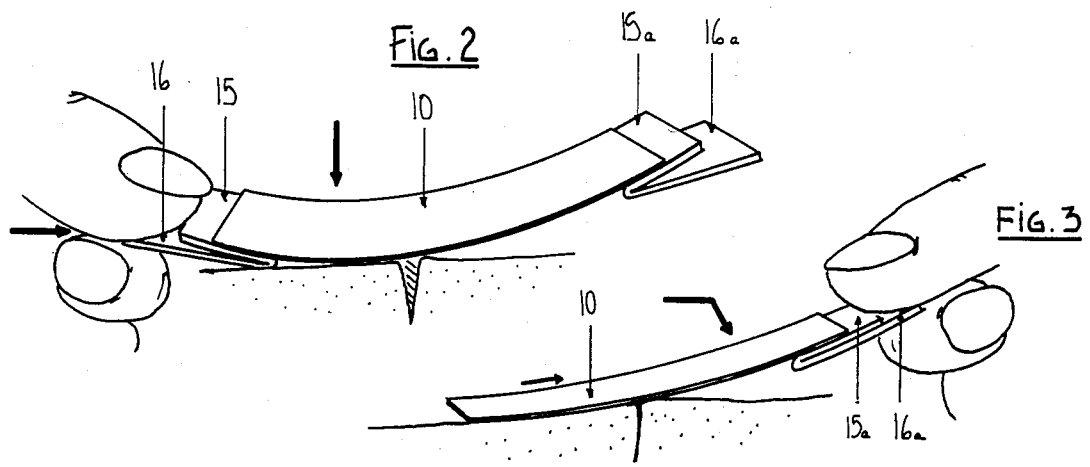
Fig. 2
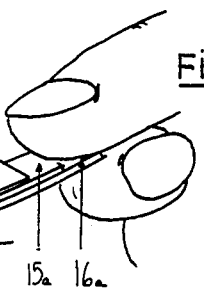
Fig. 3
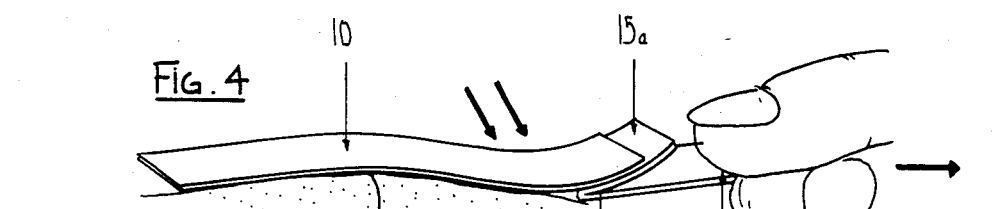
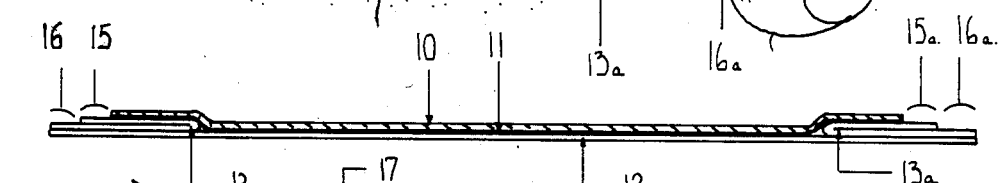
Fig. 5
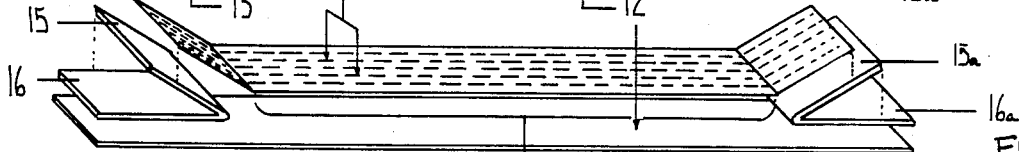
Fig. 6
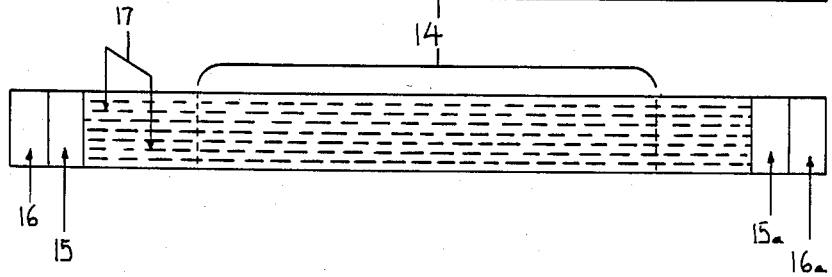
Fig. 7

SELF ADHESIVE SUTURE AND BANDAGE

BACKGROUND OF THE INVENTION

This invention relates to adhesive bandages for covering and protecting wounds and to adhesive sutures utilized to secure opposite edges of a body wound or incision together to close such incision and to retain it in closed position during healing.

Such bandages and sutures are generally formed of a suitable textile fabric provided with an adhesive backing in which the adhesive layer is covered with a protective strip of plastic material which is removed to expose the adhesive prior to application of the bandage or suture to the wound or incision. For example, in U.S. Pat. No. 3,402,716, a suture is provided in which the adhesive area is covered with a protective strip which keeps the adhesive layer sterile and in which end portions of the suture strip are not coated with adhesive to permit the unit to be handled at the ends without contact with adhesive. However, in this type of application, the protective strip must first be peeled back to expose the adhesive which requires contact with the adhesive layer and the resultant risk of contamination along with adherence of adhesive to the fingers of the person who applies the suture.

A similar structure is embodied in the commonly used, "Steri-Strip", a trademarked product of the 3M Company, which consists of a fabric strip reinforced with longitudinal filaments coated its full length with an adhesive and provided with a protective plastic sheet overlying the adhesive with the protective sheet being weakened near the ends to permit removal of end segments first to expose the adhesive at the end of the strip so that end or ends can be applied to the skin after which the remainder of the protective strip can be peeled away to permit full adhesion of the strip. In order to avoid contact of the fingers with the suture and the adhesive, it is necessary to utilize a tweezer or forceps to accomplish this. Similar problems result when such structures are utilized as wound coverings or dressings.

As shown in U.S. Pat. No. 2823672, a common type of adhesive bandage known as a "bandaid" is provided with protective strips which overlap over a central dressing pad to provide ends which can be engaged to facilitate removal from the adhesive layer; however, this arrangement leaves the central portion of the dressing exposed and requires enclosure of the entire unit in a protected cover to preserve sterility.

An interlocking suture which is described in U.S. Pat. No. 4141363 is provided with protective sheets which are peeled off from each segment but contact with the adhesive is not prevented or minimized. In one form the protective sheet is provided with an elongated end which can be grasped after it is peeled off one entire side of the tape to facilitate removal.

SUMMARY AND OBJECTS OF THE INVENTION

In accordance with the present invention, an adhesive suture or bandage structure is provided in which a central adhesive area is protected by means of a removable backing sheet with the end adhesive areas protected by a separately removable member in the form of a folded over V-shaped strip, the ends of which form tabs to be engaged by the fingers or an instrument to first permit removal of the suture from the backing sheet to be applied over the incision followed by removal of the folded tab strip from the adhesive ends of the suture. This permits removal of the suture from the protective layer and application to the incision without contact of the fingers with the adhesive layer and resultant adhesion of adhesive to fingers and possible loss of sterility. In addition, it facilitates and speeds up application of the sutures and permits application of individual suture strips at any desired distance from each other and permits more rapid wound closure.

DETAILED DESCRIPTION

In the drawings:

FIG. 1 illustrates the manner of assembly of the suture upon protective backing sheet and the manner of removal from said backing.

FIG. 2 illustrates the application of the suture to one side of an incision and the manner of removal of the protective strip at one end.

FIG. 3 illustrates the application of the suture with one end attached and preparatory to attachment of the other end with the incision closed.

FIG. 4 illustrates completion of the application of the suture with the protective tab being grasped for removal.

FIG. 5, 6 and 7 illustrate the structure and assembly of the sutures or bandages of the invention.

Referring first to the structure of the suture and to manner of assembly as shown in FIGS. 5, 6 and 7, the suture strip 10, which may be of any suitable sterile sheet material such as textile fabric or plastic, as for example, a sheet of bonded non-woven fibers as used in the well known "Steristrips", a trademarked product of the 3M Company, or of polypropylene, or other suitable textile plastic material having sufficient lateral strength. The suture strip is coated with a suitable pressure sensitive adhesive, 11, and is supported upon a protective backing sheet, 12, which may be of peelable glossy paper or thin plastic such as polyethylene. The adhesive coated strip is adhered to the backing along its central portion, 14, as shown in FIGS. 6 and 7 protected at its ends by means of folded over strip, 13, and 13a, of protective backing material such as peelable paper or plastic to form overlapping V-shaped members with superimposed projecting tabs, 15, and 16, and 15a and 16a. Preferably, the folds are such that the lower tabs, 16 and 16a are slightly longer than upper tabs, 15, and 15a, as shown.

In one preferred form of the suture or bandage, it is formed of a bonded non-woven fibrous material composed of matted rayon or polyester fibers bonded together with an adhesive and may be reinforced with longitudinal fibers or filaments of polyester or nylon or the like to provide additional longitudinal reinforcement. These fibers are shown at 17 in FIGS. 6 and 7.

Alternatively, the suture or bandage may be formed of woven fabric or of plastic film such as polypropylene, polyethylene, nylon or the like, or any material having satisfactory longitudinal strength when used as a suture, or suitable porosity and absorbence when used as a bandage. Where non-porous plastic materials are used, they may be pre-perforated to provide porosity or provided with a fibrous layer for contact with the skin to permit a degree of ventilation.

In the application of the suture strip as shown in FIGS. 1, 2, 3 and 4, the tab ends, 15 and 16 of suture 10 are grasped first at one end of the suture as shown at the left in FIG. 1, and is peeled away from the protective backing, 12. The protective tab members 13, and 13a, remain in contact with the adhesive coated ends of the suture strip. After the exposed adhesive layer is applied to the skin on one side of the wound or incision, tab end 16 is grasped and the folded member 13, is drawn away horizontally by pulling to expose the adhesive coated end portion which is then placed in contact with the skin.

The same procedure is followed at the other end while the wound or incision is kept closed as shown first in FIG. 3 and then in FIG. 4, by grasping tab 13a, and tab ends 15a and 16a as described for the first end. Optionally, the suture may be removed from the backing strip by lifting off from both ends, then applying the central adhesive area to both sides of the incision, then removing the protective tab ends as described above.

In this sequence, it is clear that the sticky ends of the suture need not be handled by fingers or instruments and sterility can be maintained even without gloves.

Although the above description has referred to the assembly and application of a single suture, in commercial production practice, it would be desirable to assemble the sutures in multiple by coating an elongated sheet of fabric with adhesive, applying elongated strips of folded over protective material at the edges and then applying a protective backing strip over the adhesive layer between the unprotected ends. This can be done batchwise or in a continuous manner. The resulting assembled layers can then be precut or preperforated to provide individual suture strips or bandages which can be removed from an assembly as desired. In an alternate procedure, a plurality of the adhesive coated fabric strips with protective folded tab end members can be formed individually and may be mounted upon sheets of protective backing material and each can then be removed from such sheets as needed.

The dimensions of the individual sutures may vary depending upon the type and size of the incision. In most cases, a plurality of suture strips may be applied while in some cases a single suture strip of desired width may be utilized. In some cases the suture strips may be cut through centrally or in half where the full length is not required. The length of the suture may vary from 3-6 inches (7.5-15.0 cm) and the width of the individual members may vary from ¼ inch (0.625 cm) to 1 inch (2.5 cm) or more. Where parallel longitudinal filaments are utilized as reinforcements, they may be spaced from 1/32 inch (1.0 mm) to 1/16 inch (2.0 mm) apart.

While the foregoing description has been applied to sutures, the folded protective members referred to may be utilized in connection with bandages where the same precautions with respect to sterility and ease of application would apply.

Other uses of the novel structure described are with respect to any self-adhesive product such as labels where application free from contact with the adhesive layer can be achieved in the same manner as described above.

I claim:

1. An adhesive member suitable for use as a surgical suture or a bandage which comprises a sheet of suture or bandage material having a self adhesive coating thereon, a removable end protective member covering either or both end portions of said adhesive coating in the form of a folded V-shaped strip having two superimposed layers the uppermost of which is adhered to and covers the end portion of the adhesive coating with both layers providing tab ends projecting beyond said ends of said sheet to provide upper and lower tabs for engagement and removal of said end protective member, said adhesive coated sheet member with with said end protective members being supported upon a removable protective backing sheet covering and protecting the adhesive coating between said end protecting members, the ends of said upper and lower tabs being engageable for sanitary removal of said strip from said backing member and the lowermost of said tabs being engageable for sterile removal of said end protecting members from the ends of said strip upon application to a treated area.

2. An adhesive member according to claim 1 wherein the sheet material is in the form of an elongated narrow strip adapted for use as a suture.

3. An adhesive member according to claim 2 wherein the sheet material is composed of bonded matted fibers.

4. An adhesive member according to claim 2 wherein the sheet material is composed of a woven fabric.

5. An adhesive member according to claim 2 wherein the sheet material is in the form of a plastic film.

6. An adhesive member according to claim 1 wherein the folded edge protecting strips are affixed with the lowermost layer projecting beyond the edge for a greater distance than the uppermost layer.

7. An adhesive member according to claim 3, wherein the sheet material in addition includes elongated spaced parallel reinforcing filaments incorporated with the bonded matted fibers.

* * * * *